United States Patent
Hamalainen et al.

(10) Patent No.: US 10,830,687 B2
(45) Date of Patent: Nov. 10, 2020

(54) MEASURING ARRANGEMENT FOR IN-LINE HOLOGRAPHY MICROSCOPY

(71) Applicant: UWater Oy, Tampere (FI)

(72) Inventors: Esa Hamalainen, Nokia (FI); Tero Kesti, Tampere (FI)

(73) Assignee: Uponor Oyj, Vantaa (FI)

( * ) Notice: Subject to any disclaimer, the term of this patent is extended or adjusted under 35 U.S.C. 154(b) by 0 days.

(21) Appl. No.: 16/310,542

(22) PCT Filed: Jun. 21, 2017

(86) PCT No.: PCT/FI2017/050464
§ 371 (c)(1),
(2) Date: Dec. 17, 2018

(87) PCT Pub. No.: WO2017/220861
PCT Pub. Date: Dec. 28, 2017

(65) Prior Publication Data
US 2019/0250559 A1    Aug. 15, 2019

(30) Foreign Application Priority Data

Jun. 22, 2016    (EP) .................................... 16175692

(51) Int. Cl.
*G01N 15/14* (2006.01)
*G03H 1/04* (2006.01)
(Continued)

(52) U.S. Cl.
CPC ....... *G01N 15/1436* (2013.01); *G01N 21/453* (2013.01); *G01N 21/85* (2013.01);
(Continued)

(58) Field of Classification Search
CPC ...... G03H 1/0005; G03H 1/00; G03H 1/0443; G03H 2001/005; G03H 2210/55;
(Continued)

(56) References Cited

U.S. PATENT DOCUMENTS

| | | | | |
|---|---|---|---|---|
| 4,243,883 A | * | 1/1981 | Schwarzmann | G01N 21/85 250/343 |
| 5,048,524 A | * | 9/1991 | Bailey | A61B 5/14535 600/327 |

(Continued)

FOREIGN PATENT DOCUMENTS

| | | |
|---|---|---|
| WO | 2010148252 A1 | 12/2010 |
| WO | 2011049965 A1 | 4/2011 |
| WO | 2012082776 A2 | 6/2012 |

OTHER PUBLICATIONS

Extended European Search Report re EP Patent Application No. 16175692.9 dated Dec. 21, 2016.

(Continued)

*Primary Examiner* — Michael P LaPage
(74) *Attorney, Agent, or Firm* — Brooks Kushman P.C.

(57) ABSTRACT

A measuring arrangement having an illuminating arrangement to emit coherent light; a cuvette defining an inner volume for receiving a fluid possibly comprising microscopic objects of foreign origin, the cuvette being arranged to receive the coherent light and let it exit therefrom through opposite entrance and exit openings, the entrance opening being closed by an entrance window. The possible microscopic objects present in the fluid scatter part of the light, the scattered and non-scattered light interfering to form interference fringes. An image sensor is configured to capture a hologram digital image frame by receiving the light propagated across the cuvette. An exit window is arranged to close the exit opening of the cuvette. The image sensor is mounted in direct contact with the cuvette.

2 Claims, 2 Drawing Sheets

(51) Int. Cl.
*G01N 21/85* (2006.01)
*G01N 33/18* (2006.01)
*G03H 1/00* (2006.01)
*G01N 21/45* (2006.01)
*G01N 15/00* (2006.01)

(52) U.S. Cl.
CPC ......... *G01N 33/18* (2013.01); *G01N 33/1826* (2013.01); *G03H 1/00* (2013.01); *G03H 1/0443* (2013.01); *G01N 2015/0065* (2013.01); *G01N 2015/1454* (2013.01); *G01N 2015/1493* (2013.01); *G03H 2001/0447* (2013.01); *G03H 2210/55* (2013.01); *G03H 2210/62* (2013.01); *G03H 2222/52* (2013.01)

(58) Field of Classification Search
CPC ........... G03H 2210/62; G03H 2222/45; G03H 2222/52; G03H 2001/0447; G01N 21/85; G01N 33/1826; G01N 21/453; G01N 15/1436; G01N 33/18; G01N 2015/1493; G01N 2015/0065; G01N 2015/1454; G01N 15/0227; G01N 2021/0378
See application file for complete search history.

(56) References Cited

U.S. PATENT DOCUMENTS

| | | | |
|---|---|---|---|
| 5,331,958 A * | 7/1994 | Oppenheimer .... | A61B 5/14535 356/39 |
| 5,385,539 A * | 1/1995 | Maynard ................ | G01N 21/51 600/322 |
| 5,601,080 A * | 2/1997 | Oppenheimer ...... | G01N 21/532 356/39 |
| 2005/0248761 A1 | 11/2005 | Nieuwenhuis et al. | |
| 2013/0222547 A1 | 8/2013 | Van Rooyan et al. | |
| 2015/0204773 A1 | 7/2015 | Ozcan et al. | |
| 2017/0220000 A1* | 8/2017 | Ozcan ................. | G03H 1/0866 |
| 2018/0168496 A1* | 6/2018 | Sato ..................... | A61B 5/0075 |
| 2019/0286053 A1* | 9/2019 | Ozcan ..................... | H04N 9/68 |

OTHER PUBLICATIONS

International Search Report re PCT/FI2017/050464 dated Sep. 20, 2017.
Sungkyu Seo et al., Lensfree Holographic Imaging for On-Chip Cytometry and Diagnostics, Lab on a Chip, vol. 9, No. 6, Jan. 1, 2009, p. 777, ISSN: 1473-0197, DOI: 10.1039/b813943a.
Jericho, S.K. et al., In-Line Digital Holographic Microscopy for Terrestrial and Exobiological Research, Planetary and Space Science 2010, vol. 58, pp. 701-705.
Zheng, G., et al., The ePetri Dish, an On-Chip Cell Imaging Platform Based on Subpixel Perspective Sweeping Microscopy (SPSM), Proceedings of the National Academy of Sciences of the USA (PNAS) Oct. 2011, vol. 108, No. 41, pp. 16889-16894.
Lee, S.A., et al., Imaging and Identification of Waterborne Parasites Using a Chip-Scale Microscope, PLOS One Feb. 2014, vol. 9, No. 2, e89712.
Mudanyali, O., et al., Water Quality Management Using a Cost-Effective and Field-Portable Lensfree On-Chip Microscope, 14th International Conference on Miniaturized Systems for Chemistry and Life Sciences, Oct. 3-7, 2010, Groningen, The Netherlands.
Mudanyali, O., et al., Detection of Waterborne Parasites Using Field-Portable and Cost-Effective Lensfree Microscopy, Lab Chip, Jul. 2010, vol. 10, pp. 2419-2423.

* cited by examiner

MEASURING ARRANGEMENT FOR IN-LINE HOLOGRAPHY MICROSCOPY

CROSS-REFERENCE TO RELATED APPLICATION

This application is the U.S. national phase of PCT Application No. PCT/FI2017/050464 filed on Jun. 21, 2017, which claims priority to EP Patent Application No. 16175692.9 filed on Jun. 22, 2016, the disclosures of which are incorporated in their entirety by reference herein.

FIELD OF THE INVENTION

The present invention relates generally to analysing fluids, such as water, by means of in-line holography microscopy. In particular, the present invention relates to a measurement or imaging arrangement for such analysis.

BACKGROUND OF THE INVENTION

Water quality is an important parameter for various applications where clean water is produced, supplied, or used. Water quality may be critical as well for the safety and health of people as end users of municipal water as for various industrial processes where water with specific quality requirements is used.

Conventionally, thorough water quality analysis has been carried out as a time-consuming laboratory process where a water sample is investigated by means of complex analysis instruments. However, for many applications, such as monitoring the water quality in water treatment plants, in municipal water supply networks, or in the internal water delivery in some critical types of residential water supply systems such as those in hospitals, elderly houses, or nurseries, as well as in certain industrial processes, much more rapid response time is necessary.

Recently, in-line holography or holographic microscopy has been proposed as one potential technology for rapid water quality monitoring. For example, a compact in-line holographic microscope for detection of pathogenic waterborne parasites is disclosed in Mudanyali O, Oztoprak C, Tseng D, Erlinger A, Ozcan A. Detection of waterborne parasites using field-portable and cost-effective lensfree microscopy. Lab on a chip. 2010; 10(18):2419-2423. Electronic publication at www.rsc.org.

In a holographic microscope apparatus, one key part is the measuring or imaging arrangement used to illuminate a target fluid volume by coherent light, and capture digital image frames by receiving the light propagated across the target fluid. The image data of the digital image frames comprise hologram patterns formed in result of interference of light scattered by the microscopic objects with non-scattered light.

Because the hologram patterns form the basis for detecting and/or determining the microscopic pattern, the reliability of the detection and/or determination may be greatly affected by the operation of the measurement or imaging arrangement. In particular, in the case of a simple arrangement with no specific optics and/or a non-sampling configuration of the arrangement allowing continuous flow-through of the fluid to be analyzed, it is important that in all situations, the measurement or imaging arrangement produces reliable image data. Reliable image data should not be affected, for example, by pressure variations in a pipe as part of which a flow-through type arrangement may be integrated.

Similarly to water quality monitoring, also various other applications exist where foreign microscopic objects in a fluid may be detected and/or analyzed by means of in-line holography microscopy.

SUMMARY OF THE INVENTION

This summary is provided to introduce a selection of concepts in a simplified form that are further described below in the Detailed Description. This Summary is not intended to identify key features or essential features of the claimed subject matter, nor is it intended to be used to limit the scope of the claimed subject matter A measuring arrangement for in-line holography microscopy is disclosed which may be used for detecting microscopic objects of foreign origin present in a fluid. Such detecting may be utilized, for example, for monitoring water quality in water supply, distribution, or use systems and networks wherein the microscopic objects may be, for example, impurity particles and/or microbes. Alternatively, the fluid may be some other liquid or gas.

"In-line holography microscopy" refers to analysis and measurement procedures where one or more digital image frames of a sample volume, illuminated by coherent light, are captured, the digital image frame(s) comprising hologram patterns resulting from microscopic objects of foreign origin present in the sample volume. However, "in-line holography microscopy" also covers analysis and measurement procedures where no complete reconstruction of the sample volume is calculated or generated on the basis of the digital image frame(s) comprise hologram patterns hologram patterns, but determinations concerning the content of the sample volume are made on the basis of the captured digital image frame(s).

The apparatus may comprise an illuminating arrangement configured to emit coherent light; a cuvette defining an inner volume for receiving a fluid possibly comprising microscopic objects of foreign origin, the cuvette being arranged to receive the coherent light and let it, after propagating across the cuvette, exit therefrom through opposite entrance and exit openings, respectively, the entrance opening being closed by an entrance window whereby the possible microscopic objects present in the fluid scatter part of the light, the scattered and non-scattered light interfering so as to form interference fringes behind the microscopic objects; an image sensor comprising a light sensitive cell, the image sensor being arranged to capture a hologram digital image frame by receiving the light propagated across the cuvette; and an exit window arranged to close the exit opening of the cuvette.

Advantageously, the image sensor may be mounted in the arrangement in direct contact with the cuvette.

Many of the attendant features will be more readily appreciated as the same becomes better understood by reference to the following detailed description considered in connection with the accompanying drawings.

BRIEF DESCRIPTION OF THE DRAWINGS

The present description will be better understood from the following detailed description read in light of the accompanying drawings, wherein.

DETAILED DESCRIPTION

Figure 1:
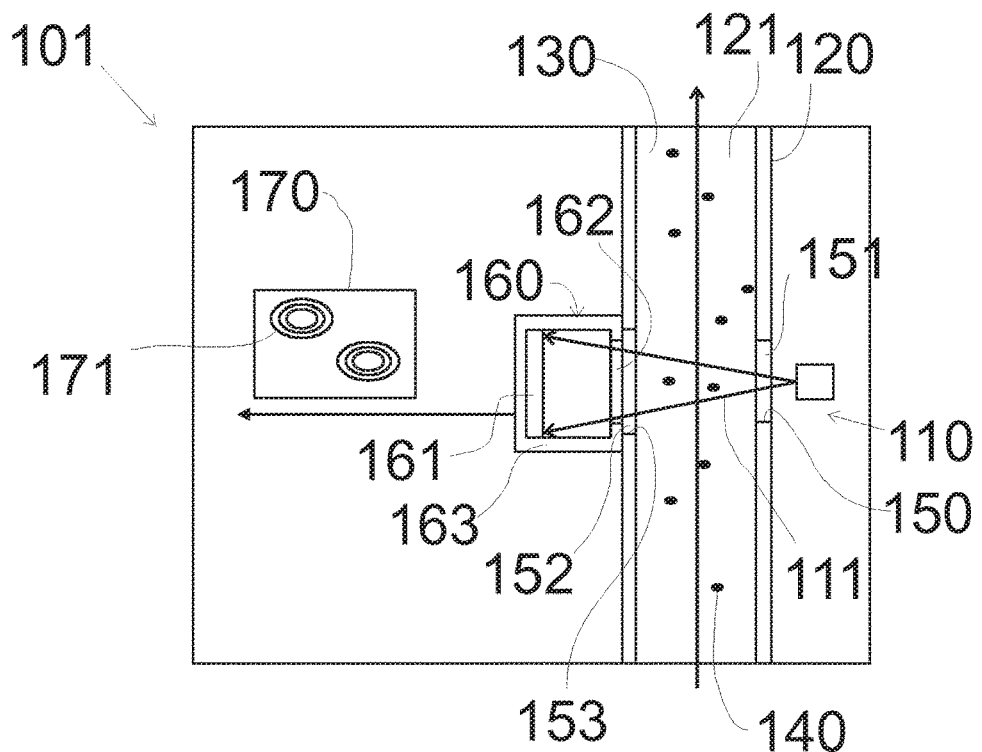
FIGS. 1 to 3 illustrate, as schematic drawings, measuring arrangements for detecting microscopic objects of foreign origin present in a fluid.

The measurement arrangement (101) of FIG. 1 is suitable, and may be used, for in-line holography microscopy.

"In-line holography microscopy" refers to investigation methods and apparatuses by which a microscopic object of foreign origin present in fluid illuminated by coherent light may be detected and/or determined on the basis of a hologram pattern formed by interference of a portion of the light scattered forward by such objects with non-scatted portion of the light.

The expression "of foreign origin" refers to that the microscopic objects are not formed of the fluid itself. They may originate, for example, from the materials of pipes or containers in which the fluid at issue is conveyed or stored. Particles of the materials of such systems may be released to the fluid, for example, in result of a pipe breakage or equipment failure. Alternatively, microscopic objects of foreign origin may originate from foreign bodies or contaminants ended up within such pipes or containers. In the case of water supply systems, for example, such foreign body producing microbes into the fluid may be a dead animal.

In the case of water supply, distribution, or use systems and networks, microbes not normally present may be, for example, various bacteria, such as bacteria belonging to coliform or *Legionella* groups, protozoa such as *Giardia lamblia*, or various types of algae.

On the other hand, from the physical properties point of view, "microscopic objects of foreign origin" have typically, for example, a refractive index differing from that of the fluid. This enables detection of such objects by means of optical sensing. In the measuring arrangement of FIG. 1, this is utilized in that the detection of the microscopic objects is based on scattering of light by the microscopic objects due to the difference between the refractive indices of the microscopic objects and the fluid.

From dimensional point of view, "microscopic objects" refer to objects having their characteristic dimensions, such as maximum diameter, length, or width, in the range of 0.1, 0.5 or 1.0 to 50 or 100 μm. Objects with so small characteristic dimensions are not visible to human eye, so they cannot be detected visually. On the other hand, holograms formed by that sized objects are detectable by image sensor having a reasonably small size. Further, with such micrometer scale characteristic dimensions, objects scatter light mainly forward, thereby enabling efficient detection by in-line holography.

The measuring arrangement comprises an illuminating arrangement 110 which emits, when in use, coherent light 111. The light may be emitted, for example, as short pulses.

Further, the measuring arrangement comprises a cuvette 120 which defines an inner volume 121 for receiving a fluid 130 which may comprise microscopic objects 140 of foreign origin.

"Cuvette" refers to a structure of any appropriate type suitable for defining an inner volume for receiving a fluid to be measured and/or analyzed by measurement system arranged in connection with the cuvette. A cuvette may comprise one or more walls defining the inner volume thereof. Defining the inner volume means that the one or more walls limit or surround a cross-section of the inner volume throughout a perimeter thereof. In other words, the one or more walls and/or some other appropriate structure of the cuvette completely encircles the entire inner volume at least at one cross-section thereof, thereby preventing escaping of the fluid to me measured from the inner volume in directions in the plane of such cross-section.

A cuvette may be of sampling type, in which case a discrete sample volume may be contained in such inner volume. Alternatively, a cuvette may be of flow-through type allowing the fluid to be measured or analyzed to flow continuously through the cuvette during the measurements. In some embodiments, a cuvette may be configured to serve alternatively as a sampling type cuvette or as a flow-through cuvette.

The cuvette comprises an entrance opening 150 closed by an entrance window 151, so positioned relative to the illuminating arrangement that when in use, the cuvette receives the coherent light emitted by the illuminating arrangement through the entrance window.

The cuvette has also an exit opening 153 closed by an exit window 152 mounted to the cuvette wall and forming a part of the cuvette, opposite to the entrance window, through which the cuvette lets light received into the cuvette, after propagating across the cuvette, exit therefrom.

"Mounting" refers to attaching or fixing, releasably or non-releasably, a component, element, or module to another structure. Mounting may be made, for example, by glue or any other appropriate type of adhesive.

When illuminating the fluid in the cuvette by the coherent light, the possible microscopic objects present in the fluid scatter part of the light forward, and the scattered and non-scattered portions of light interfere so that interference fringes are formed behind the microscopic objects.

Emitting of and illuminating by "coherent light" refers to at least part of the emitted light and the light by which the sample volume is illuminated being spatially and temporally sufficiently coherent so that said interference is possible. Thus, emitting coherent light and illuminating by coherent light does not exclude the possibility of emitting also non-coherent light nor illuminating the sample volume also by non-coherent light. Thus, light emitted by the illuminating arrangement, and light by which the sample volume is illuminated may comprise coherent and non-coherent light. In this sense, "coherent light" refers to "at least partially coherent light".

"Behind" refers to the locations of the interference fringes as observed from the direction of incidence of the illuminating light, i.e. the coherent light by which the fluid is illuminated. In other words, when observed from the location of a light source producing the coherent light, the interference fringes are formed mainly behind the microscopic objects, i.e. at the side of the microscopic objects opposite to the side from which the coherent light is incident on the microscopic objects.

The illuminating arrangement may comprise any appropriate light source, such as a laser diode, capable of producing coherent light. The light may have wavelength(s), for example, in the range of 350 to 500 nm, without being limited to that range. The illuminating arrangement may further comprise any appropriate optical elements configured to guide the emitted coherent light towards the cuvette to illuminate the fluid received therein.

The measuring arrangement 101 of FIG. 1 further comprises an image sensor 160 comprising a light sensitive cell 161 and a transparent protective window 162, through which the light can enter the image sensor, positioned in front of the light sensitive cell. The light sensitive cell is enclosed in a housing 163, a part of which the protective window forms.

The illuminating arrangement and the image sensor are positioned at opposite sides of the cuvette to form a direct propagation path of light from the illuminating arrangement to the image sensor via the cuvette. The image sensor is positioned and configured to capture a hologram digital image frame 170 by receiving the light propagated across the cuvette and exiting it through the exit window 152.

In other embodiments, indirect optical configurations may be implemented where light is guided to the image sensor, for example, via one or more mirrors.

"An image sensor" refers to a light detecting component or element capable of capturing digital image frames. An image sensor may comprise, for example, a CMOS (Complementary Metal Oxide Semiconductor) or CCD (Charge-Coupled Device) light sensitive cell or any other appropriate type of a light sensitive cell as an active, light detection imaging element.

The image sensor may be, for example, a black and white type sensor, a greyscale sensor, or a monochrome type sensor. Suitable size of the active area and the resolution of the light sensitive cell depend on the overall configuration of the measuring arrangement. In some embodiments, it may have, for example, a size of 5×5 mm². In some embodiments, the active area of the light sensitive cell may have, for example, 5 million pixels.

A "digital image frame", or shortly a "frame", refers to a data content captured via exposure of pixels or some other light-sensing element(s) of a light sensitive cell of an image sensor. A frame thus generally comprises image data enabling composition of a displayable digital image on the basis of that image data. Image data of a digital image frame may comprise, for example, information about light energy received by pixels of an image sensor.

When capturing the hologram digital image frame 170, the interference fringes formed by the scattered and non-scattered light behind the microscopic objects possibly present in the fluid form hologram patterns 171 with spatially alternating intensity formed by the interference fringes on the light sensitive cell of the image sensor. Those hologram patterns are then contained in the image data of the captured hologram digital image frame.

On the basis of such hologram patterns, the presence of the microscopic objects of foreign origin in the fluid may be detected. Further, also some properties, such as the size and the shape thereof, may also be determined.

The cuvette of the measuring arrangement of FIG. 1 is of flow-through type, wherein continuous flow of the fluid 130 to be analyzed may be led through the cuvette along its longitudinal direction during the analysis. In other embodiments, cuvette of other types may be used, which are based on any appropriate type of sample cell or container capable of receiving the fluid to be analyzed. For example, a cuvette may be of sampling type, wherein a discrete volume may be stored in the cuvette for the analysis. Such cuvette may comprise one or more inlet/outlet openings for filling and emptying the cuvette by the fluid to be analyzed.

As stated above with reference to the example of FIG. 1, "flow-through" type of a cuvette refers to a configuration of the cuvette allowing continuous flow of a fluid through the cuvette while carrying out the measurement of the fluid flowing through the cuvette.

In the measuring arrangement of FIG. 1, the illuminating arrangement is directed crosswise relative to the flowing direction of the fluid flowing in the flow-through type cuvette. Thereby, the flow is directed correctly relative to the illuminating direction.

A cuvette and a measuring arrangement as a whole may have any appropriate dimensions, taking into account the application at issue. For example, in the measuring arrangement of FIG. 1, the thickness of the inner volume in the illuminating direction may be, for example, in the range of 0.5 to 1 mm. The width of the cuvette may be adjusted, for example, on the basis of the size of the light sensitive cell of the image sensor which may lie, for example, at a distance of about 1 to 3 mm from the inner volume of the cuvette. For example, the cuvette may have, in one or more directions, a width of 4 to 8 mm. One pixel of the light sensitive cell may have a width, for example, in the range of 1.5 to 5 µm. For example, the width of a rectangular pixel may be about 2 µm. The positioning of the light source of the illuminating arrangement may vary depending on, for example, on the light source and the size of the light emitting surface thereof. In an example, a laser diode as a light emitting element of a light source may be positioned at some tens of millimeters, for example about 40 mm, from the inner volume of the cuvette.

In the measuring arrangement 101 of FIG. 1, the protective window 162 of the image sensor and thereby the image sensor is in direct contact with the exit window 152, which in turn is mounted to the cuvette and forms an integral part of it. Thereby, the image sensor is mounted in direct contact with the cuvette.

Said direct contact may be formed by mounting of the image sensor to the cuvette via the casing 163 enclosing the light sensitive cell. Alternatively, or additionally, the protective window may be mounted to the exit window by means of an adhesive, such as an optically clear adhesive (OCA), which may be applied between the protective window and the exit window. Such adhesive may be selected not to substantially affect the propagation of light through the stack of the exit window and the protective window.

The image sensor being in direct contact with the cuvette means, generally, that there is no freely accessible space between the image sensor and the inner volume defined by the cuvette. In the measuring arrangement of FIG. 1, there is thus no such space between the exit window of the cuvette and the protective window of the image sensor. This may be advantageous in that no contaminants can adhere in the outer surfaces of the protective window and the exit window, which contaminants might disturb sensing the hologram patterns by the image capturing.

Second, the coherent light, as illustrated in the example of FIG. 1, may be emitted or guided into an expanding cone or beam. Alternatively, it may be emitted or guided into a collimated beam. In the former case, the interference fringes may be expanded as function of the distance from the scattering microscopic objects. Further, irrespective of whether the illuminating light is emitted or guided into an expanding or into a collimated light beam, the interference fringes expand due to the scattering of the light into various directions, depending on the types of the microscopic objects and the wavelength of the illuminating light. Consequently, the longer the distance between a microscopic object and the image sensor, the larger is the expanding cone or beam, and also the hologram pattern formed on the image sensor. To keep the required size of the light sensitive cell reasonably small, it may be desirable to have the light sensitive cell of the image sensor as close to the inner volume of the cuvette as possible. Generally, the image sensor being in direct contact with the cuvette, thus the protective window being in direct contact with the exit window of the cuvette in the measuring arrangement of FIG. 1, serves for this purpose.

Third, in the case of a flow-through type cuvette as that of FIG. 1, the cuvette may be connected to an external piping from which the fluid to be analyzed is led to the cuvette as a continuous flow. In such case, possible pressure variations in such piping may be transmitted to the cuvette also. The protective window in direct contact with the exit window of the cuvette in the measuring arrangement in FIG. 1 may strengthen the exit window, thereby preventing it from adverse bending in response to possible pressure variations, which bending might change the optical path between the cuvette and the image sensor.

Figure 2:
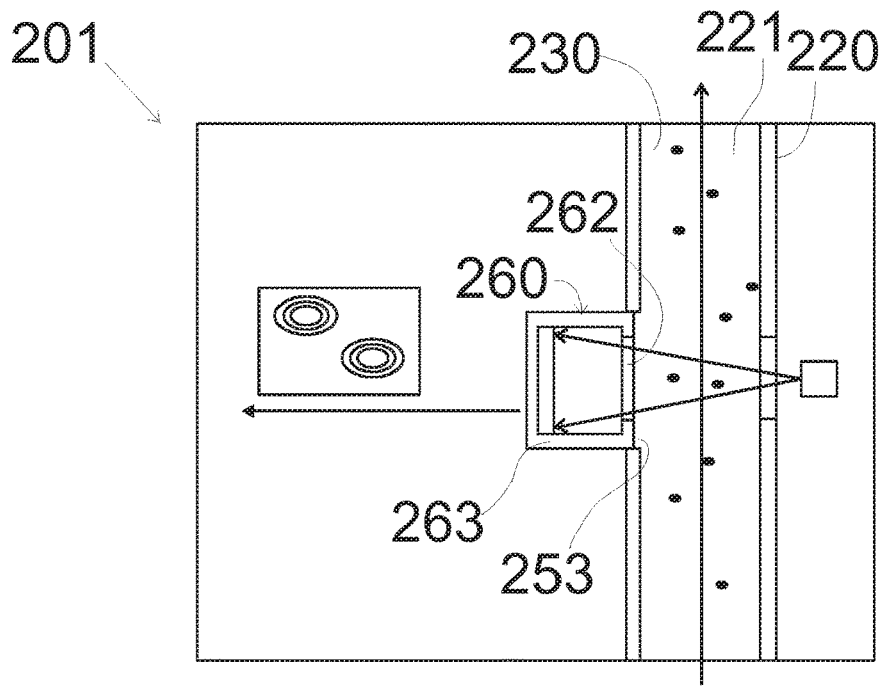

The measuring arrangement 201 of FIG. 2 differs from that of FIG. 1 in that there is no separate exit window in the cuvette. Instead, the cuvette wall has an exit opening 253 into which the image sensor 260 is inserted and via which the housing 263 of the image sensor is mounted to the cuvette 220.

In the measuring arrangement of FIG. 2, the protective window 262 of the image sensor thus forms, or serves as, an exit window through which the light propagated across the cuvette 220 may exit therefrom.

In the measuring arrangement 201 of FIG. 2, the protective window 262 of the image sensor 260 is in direct contact with the cuvette and the inner volume 221 of the cuvette and the fluid 230 present therein.

Figure 3:
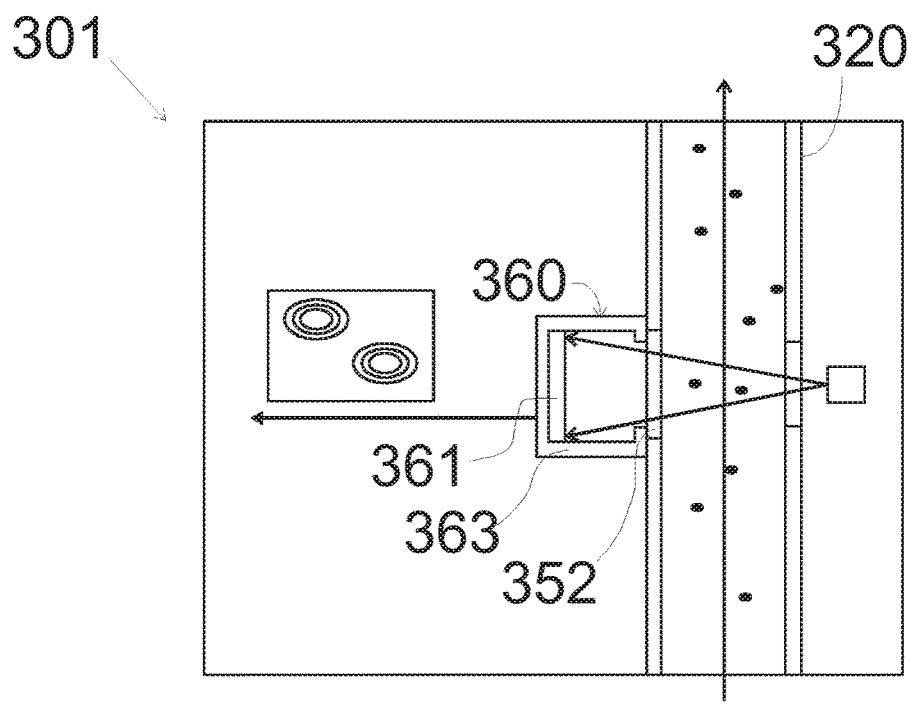

The measuring arrangement 301 of FIG. 3 differs from that of FIG. 1 in that the image sensor 360 does not comprise separate protective window. Instead, the exit window 352 of the cuvette 320 forms, or serves as, also as a protective window protecting the light sensitive cell 361 and enclosing the casing 363 of the image sensor. Thereby, the image sensor is mounted in direct contact with the cuvette.

In other embodiments where an image sensor with no separate protective window is mounted to a cuvette to which an exit window is mounted, the image sensor may be implemented without any casing. For example, the light sensitive cell may be mounted on a substrate and encapsulated by an encapsulating material via which the image sensor may be mounted to the exit window.

Any of the measuring arrangements of FIGS. 1 to 3 may be used in a complete detecting apparatus comprising, in addition to the measuring arrangement, also a computing arrangement configured to detect the presence of the microscopic objects on the basis of hologram patterns formed by the interference fringes in the image data of the hologram digital image frames.

Said detection may be based on reconstructing one or more two-dimensional images of the illuminated fluid volume in accordance with principles and processes as such known in the field of holographic microscopy.

Figure 4:
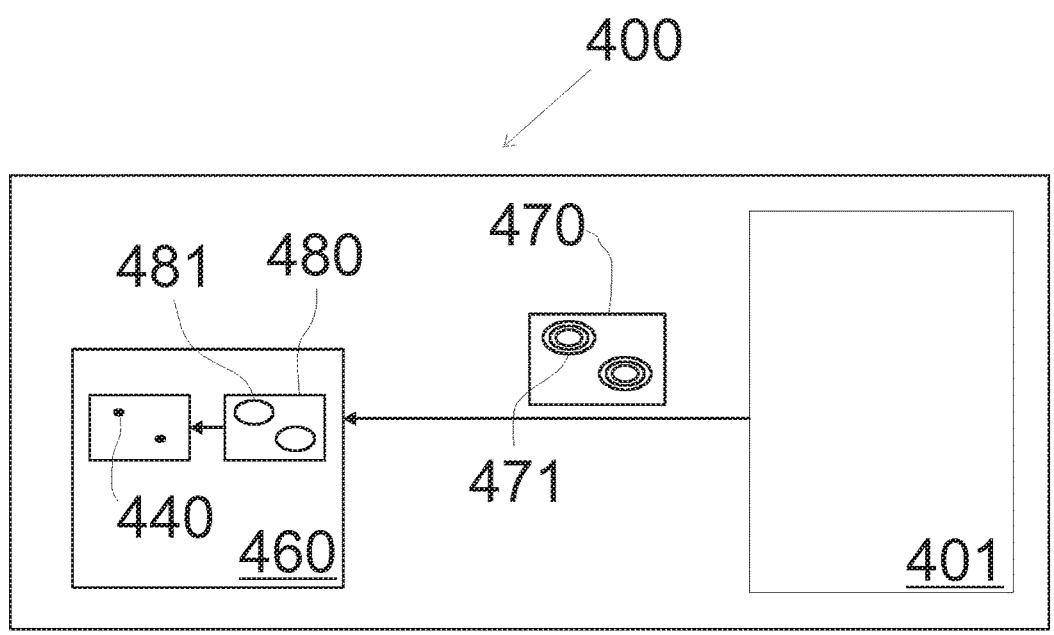
FIG. 4 illustrates, as a schematic block diagram, an apparatus for detecting microscopic objects of foreign origin present in a fluid.

Alternatively, such detection may be carried out on the basis of the hologram patterns present in the image data of the captured hologram digital image frame(s). The apparatus 400 of FIG. 4 represents one embodiment of this type.

The apparatus 400 has a measuring arrangement 401 which may be in accordance with any of the measuring arrangements discussed above with reference to FIGS. 1 to 3.

The measuring arrangement produces, when in use, hologram digital image frames 470 which may comprise hologram patterns 471 formed due to possible presence of microscopic objects of foreign origin in the fluid to be analyzed.

The measuring arrangement further comprises a computing arrangement 460 connected to the measurement arrangement 401 to receive image data of the captured hologram digital image frames, and to detect the presence of the microscopic objects on the basis of the hologram patterns 471 formed by the interference fringes in the image data of the hologram digital image frames 470.

In the example of FIG. 4, the computing arrangement may be configured to pre-process the received image data of the hologram digital image frame by any appropriate data processing operations facilitating the detection of the microscopic objects on the basis of the hologram patterns.

The computing arrangement is further configured to provide filtered image data 480, comprising automatically filtering, for example, the received and possibly pre-processed image data by a symmetric edge detection algorithm, at least in two different directions, the filtered image data comprising, for each hologram pattern 471 present in the received image data, a filtered hologram pattern 481. In said filtering, for example, any appropriate convolution kernel may be used.

As known for a skilled person, there are a great variety of known mathematical operations which may be used to filter image data for edge detecting purposes. Generally, the principle in edge detection is to find out, by filtering image data by such edge detection algorithms, where there are relatively abrupt changes in the image content. For example, the parameter of interest used to find "edges" may be the intensity of light received by the image sensor during capture of the frame, i.e. the brightness of the image formed by the image data.

In result of filtering image data by an edge detecting algorithm, the filtered image data generally highlights the edges, i.e. contours of distinguishable objects present in the original image data. In the case of filtering the received image data 470 with the hologram patterns 471, the filtered image data thus comprises the contours of the original hologram patterns in the form of the filtered hologram patterns 381.

On the basis of the filtered hologram patterns, further analysis of the image data can be focused on, or limited to, the actual locations of the holograms in the image area. Great savings in the required computing power may then be saved because the rest of the image data does not need to be analyzed.

"Symmetry" of the edge detection algorithm refers to edge detection algorithms designed not to substantially change the shape of the objects in the image area in result of the filtering.

Finally, the computing arrangement is configured to automatically detect, on the basis of the filtered hologram patterns, the presence of the microscopic objects 440 associated with the filtered hologram patterns in the sample volume of the fluid.

Thus, possible filtered hologram patterns of the filtered image data are used as indication of the presence of microscopic, scattering objects in the fluid contained in the cuvette.

Detecting the presence of microscopic objects refers to determining whether there are any microscopic objects in the fluid. In this sense, detecting the presence of such objects may also comprises determining and concluding that there is no such object present in the fluid volume through which the illuminating light propagated to the image sensor. On the other hand, when there is a plurality of filtered hologram patterns in the filtered image data, said detection may naturally comprise, in addition to determine the general presence of the microscopic objects, also the number of them in the analyzed fluid volume.

The result of the detection operation, i.e. the information about the presence of microscopic objects in the analyzed fluid volume, may be arranged in any appropriate electric data or signal form suitable for storage or transmitting further.

The computing arrangement may comprise any appropriate data processing and communicating equipment, unit(s), element(s), and component(s) capable of carrying out the operations of the method discussed above.

From another terminology point of view, a computing arrangement "configured to" perform a specific method operation means that the computing arrangement comprises, or serves as, "means for" performing that operation.

The computing arrangement may comprise separate means for different operations. Alternatively, any of such means for performing those various operations specified above may be combined so that more than one operation is carried out by the same means. It is even possible that all those operations are carried out by the same means, e.g. by a single data processing module or unit.

Any means for performing any of the above operations may comprise one or more computer or other computing and/or data processing components, units, devices, or apparatuses. In addition to actual computing and/or data processing means, the means for performing said operations may naturally also comprise any appropriate data or signal communication and connecting means, as well as memory or storage means for storing generated and/or received data.

Computing and/or data processing means serving as means for performing one or more of the above operations may comprise, for example, at least one memory and at least one processor coupled with the at least one memory. Then, the at least one memory may comprise computer-readable program code instructions which, when executed by the at least one processor, cause the apparatus to perform the operation(s) at issue.

In addition to, or instead of, a combination of a processor, a memory, and program code instructions executable by the processor, means for performing one or more operations may comprise some hardware logic components, elements, or units, such as those examples mentioned above with reference to the method aspect.

The apparatus 400 of FIG. 4 may be implemented as stand-alone apparatus or sensor. Alternatively, it may form a part of a larger controlling or monitoring system.

It is to be noted that the present invention is not limited to the embodiments and examples above. Instead, the embodiments of the present invention can freely vary within the scope of the claims.

It will be understood that the benefits and advantages described above may relate to one embodiment or example or may relate to several embodiments or examples. The embodiments and examples are not limited to those that solve any or all of the stated problems or those that have any or all of the stated benefits and advantages. It will further be understood that reference to 'an' item refers to one or more of those items.

The term "comprising" is used in this specification to mean including the feature(s) or act(s) followed thereafter, without excluding the presence of one or more additional features or acts.

The invention claimed is:

1. A measuring arrangement for in-line holography microscopy, comprising:
an illuminating arrangement configured to emit coherent light;
a flow-through cuvette defining an inner volume for receiving a flow of fluid to be checked for the presence of microscopic objects of foreign origin, the cuvette being arranged to receive the coherent light and let it, after propagating across the cuvette, exit therefrom through opposite entrance and exit openings, respectively, the entrance opening being closed by an entrance window, whereby the microscopic objects when present in the fluid scatter part of the light, the scattered and non-scattered light interfering so as to form interference fringes behind the microscopic objects;
an image sensor comprising a light sensitive cell, the image sensor being arranged to capture a hologram digital image frame by receiving the light propagated across the cuvette; and
an exit window arranged to close the exit opening of the cuvette;
wherein:
the image sensor is mounted in direct contact with the cuvette;
the exit window is mounted to the cuvette, and the image sensor comprises a protective window positioned in front of the light sensitive cell, the protective window being mounted to the exit window; and
the cuvette is configured to be connected to an external piping to allow flow of the fluid from the external piping through it continuously during the measurements.

2. An apparatus comprising a measuring arrangement as defined in claim 1, and a computing arrangement connected to the measurement arrangement to receive image data of the hologram digital image frame, and to detect the presence of the microscopic objects on the basis of hologram patterns formed by the interference fringes in the image data of the hologram digital image frame.

* * * * *